US009510919B2

(12) United States Patent
Kim

(10) Patent No.: US 9,510,919 B2
(45) Date of Patent: Dec. 6, 2016

(54) TOOL FOR BONDING ORTHODONTIC BRACKET

(71) Applicant: Joong Han Kim, Seoul (KR)

(72) Inventor: Joong Han Kim, Seoul (KR)

( * ) Notice: Subject to any disclaimer, the term of this patent is extended or adjusted under 35 U.S.C. 154(b) by 112 days.

(21) Appl. No.: 14/375,796

(22) PCT Filed: Jan. 31, 2013

(86) PCT No.: PCT/KR2013/000814
§ 371 (c)(1),
(2) Date: Jul. 31, 2014

(87) PCT Pub. No.: WO2013/115588
PCT Pub. Date: Aug. 8, 2013

(65) Prior Publication Data
US 2015/0056565 A1    Feb. 26, 2015

(30) Foreign Application Priority Data

Jan. 31, 2012   (KR) ........................ 10-2012-0009813

(51) Int. Cl.
*A61C 7/02*   (2006.01)
*A61C 7/04*   (2006.01)
(Continued)

(52) U.S. Cl.
CPC . *A61C 7/02* (2013.01); *A61C 7/04* (2013.01); *A61C 7/146* (2013.01); *A61C 7/16* (2013.01)

(58) Field of Classification Search
CPC ............... A61C 3/10; A61C 3/16; A61C 7/04; A61C 7/146; A61C 7/02
(Continued)

(56) References Cited

U.S. PATENT DOCUMENTS 4,035,919 A    7/1977  Cusato
4,184,259 A *  1/1980  Sosnay .................... A61C 7/04
                                                       140/106

(Continued)

FOREIGN PATENT DOCUMENTS

| KR | 10-0163827    | 12/1998 |
| KR | 10-0419444    | 2/2004  |
| WO | WO 2013/115588 | 8/2013  |

OTHER PUBLICATIONS

International Search Report Dated May 9, 2013 From the Korean Intellectual Property Office Re. Application No. PCT/KR2013/000814 and Its Translation Into English.

*Primary Examiner* — Nicholas Lucchesi

(57) ABSTRACT

The present invention relates to a tool for adhering an orthodontic bracket, comprising: a pair of bracket holding portions for holding a bracket to be bonded to teeth while approaching or separating from each other; and a pair of handle portions connected to the pair of bracket holding portions, for controlling the bracket holding portions to allow the same to approach or separate from each other, wherein a scale for measuring the height of a bracket for the end of teeth is formed in at least any one of the pair of bracket holding portions. Therefore, an operation is convenient, measurement is easy and measurement time can be reduced since the tool has a simple and uncomplicated structure. In addition, it is possible to improve the effectiveness of orthodontic treatment since a bracket can be bonded by precisely setting the height of the bracket.

8 Claims, 7 Drawing Sheets

(51) Int. Cl.
*A61C 7/16* (2006.01)
*A61C 7/14* (2006.01)

(58) Field of Classification Search
USPC .......................................................... 433/3, 4
See application file for complete search history.

(56) References Cited

U.S. PATENT DOCUMENTS

| | | | |
|---|---|---|---|
| 4,626,208 A | 12/1986 | Hall | |
| 4,708,651 A * | 11/1987 | Buchanan | A61C 19/04 433/102 |
| 5,007,827 A * | 4/1991 | DiFranco | A61C 7/146 294/99.2 |
| 5,261,813 A * | 11/1993 | Baker | A61C 7/02 433/157 |
| 6,776,615 B2 * | 8/2004 | Dietrich | A61C 3/10 433/159 |
| 6,783,359 B2 * | 8/2004 | Kapit | A61C 7/146 433/141 |
| 6,786,719 B2 * | 9/2004 | McGann | A61C 7/146 433/4 |
| 7,621,742 B2 * | 11/2009 | Michaelson | A61C 3/10 294/99.2 |
| D638,322 S * | 5/2011 | Teramoto | A61C 7/146 D10/73 |
| 8,088,142 B2 * | 1/2012 | Yamada | A61B 17/0057 606/210 |
| 8,979,531 B2 * | 3/2015 | Mueller | A61C 3/10 433/162 |
| 2001/0018175 A1 * | 8/2001 | Kim | A61C 7/145 433/4 |
| 2002/0006595 A1 * | 1/2002 | Voudouris | A61C 7/02 433/4 |
| 2003/0134250 A1 * | 7/2003 | McGann | A61C 7/146 433/4 |
| 2011/0003263 A1 * | 1/2011 | Clor | A61C 7/146 433/4 |

* cited by examiner

TOOL FOR BONDING ORTHODONTIC BRACKET

RELATED APPLICATIONS

This application is a National Phase of PCT Patent Application No. PCT/KR2013/000814 having International filing date of Jan. 31, 2013, which claims the benefit of priority of Korean Patent Application No. 10-2012-0009813 filed on Jan. 31, 2012. The contents of the above applications are all incorporated by reference as if fully set forth herein in their entirety.

TECHNICAL FIELD

The present invention relates to an orthodontic bracket attaching tool, and more particularly, to an orthodontic bracket attaching tool that can conveniently perform a surgical operation and can easily perform measurement due to a simple structure and that can shorten a measurement time and that can attach a bracket by accurately setting a height of the bracket and that can thus improve orthodontic efficiency.

BACKGROUND ART

In general, a most important step of an orthodontic treatment field that recovers an aesthetic function, a pronunciation function, and a mastication function of teeth by regularly arranging teeth is to quickly and accurately attach a bracket in a specific portion of teeth, but to locate the bracket at a uniform and harmonic height with adjacent teeth.

By inserting an orthodontic wire that provides elasticity that moves teeth into a slot of a well attached bracket, an orthodontic force thereof is transferred to teeth, and thus a desired teeth movement can be performed.

Therefore, when performing an orthodontic treatment, a method and a device for attaching a bracket are very important.

In such an orthodontic treatment, when a bracket is accurately located, i.e., when an appropriate vertical height and angulation (a slope of a near and far direction (lateral direction) of teeth, a torque (a slope of a labial-lingual direction (front-rear direction) of teeth), and a rotation (rotation level of a teeth mounting reference) are three-dimensionally precisely performed in teeth, a good orthodontic treatment is guaranteed, and in this case, particularly, when a height determined by a surgical operation of a surgical operator is wrongly set, angulation and rotation including a torque may be also deformed and thus appropriate height setting is regarded as a very important orthodontic treatment process.

Conventionally, a bracket has been attached at a bracket mounting location of teeth using an adhesive while depending on a surgical operator's naked eye.

In this way, when mounting a bracket depending on naked eye, there is a defect that an attaching location of the bracket is not uniform and inaccurate.

In order to solve such a defect, nowadays, a method of attaching a bracket using a gauge is used, as disclosed in Korean Patent Application No. 10-2006-0135828.

However, at the conventional art including the document, by measuring a distance between an end portion of teeth and a slot of a bracket using a separate gauge, it should be measured whether the bracket is accurately attached to teeth, measurement should be performed within a narrow slot in view of a gauge structure and thus a surgical operation is difficult, and when attaching the bracket, it is difficult to maintain horizontality so as to measure a vertical height to a tooth end portion and a bracket slot on another plane, and particularly, there is a problem that it is difficult to maintain horizontality of a molar area allowing a narrow visual field and different to approach. Further, it is difficult to extend a surgical operation time in a dual process of firstly holding a bracket to which an adhesive to be hardened within several seconds is applied with a tweezer and temporally attaching the bracket on a tooth surface and of secondly measuring a height using a gauge.

Finally, in the conventional art, because it is not easy to accurately set an end portion of teeth and a height of a bracket, technology development that supplements such a defect is requested.

DETAILED DESCRIPTION OF INVENTION

Technical Problem

The present invention has been made in view of the above problems, and provides an orthodontic bracket attaching tool that can conveniently perform a surgical operation due to a simple structure and in which measurement can be easily performed because measurement is performed from an end portion of a bracket base on the same plane as that of an end portion of teeth to an end portion of teeth and in which horizontality can be easily maintained and that can save a time because a tweezer and a measuring gauge function are simultaneously performed and that can fix the bracket by accurately setting a height of the bracket and that can thus improve orthodontic efficiency.

Technical Solution

In accordance with an aspect of the present invention, an orthodontic bracket attaching tool includes: a pair of bracket holding portions that hold a bracket to be attached to teeth while approaching each other or separating from each other; and a pair of handle portions connected to the pair of bracket holding portions to manipulate the bracket holding portion to approach each other or separate from each other, wherein in an end portion of at least one of the pair of bracket holding portions, a scale that measures a height of the bracket to an end portion of the teeth is formed, and an end portion indication portion that indicates an end portion of the teeth is installed.

Preferably, the bracket holding portion has a quadrangular section shape.

Preferably, the bracket holding portion is disposed at an end portion of the teeth to have a polygonal section shape in which a latch jaw that forms a measurement reference is formed, and in the bracket holding portion, an end portion indication portion that indicates an end portion of the teeth is formed.

Preferably, the scale is formed in at least one side of the bracket holding portion.

Preferably, the bracket includes: a bracket base to which an adhesive is attached: a slot into which an orthodontic wire is inserted; and a stem disposed between the bracket base and the slot, wherein the bracket holding portion in which the scale is formed measures a distance between one side of the bracket base or the stem and the teeth end portion.

Preferably, the orthodontic bracket attaching tool further includes a guide that guides an approaching or separating operation of the pair of bracket holding portions.

Preferably, the guide includes: a first guide provided in an area of the pair of bracket holding portions; and a second guide provided in an area of the pair of handle portions.

Preferably, both the first and second guides each include: a guide protrusion; and a guide groove that guides the guide protrusion.

Preferably, the bracket holding portion has a stepped polygonal shape having a width that reduces or enlarges as advancing to an end portion or a protruded shape having a protruded one side.

Advantageous Effects

According to the present invention, due to a simple structure, a surgical operation can be conveniently performed and measurement can be easily performed, a measurement time can be shortened, a bracket can be attached by accurately setting a height thereof, and orthodontic efficiency can be thus improved.

BEST MODES FOR CARRYING OUT THE INVENTION

Hereinafter, an exemplary embodiment of the present invention will be described in detail with reference to the accompanying drawings.

Figure 1:
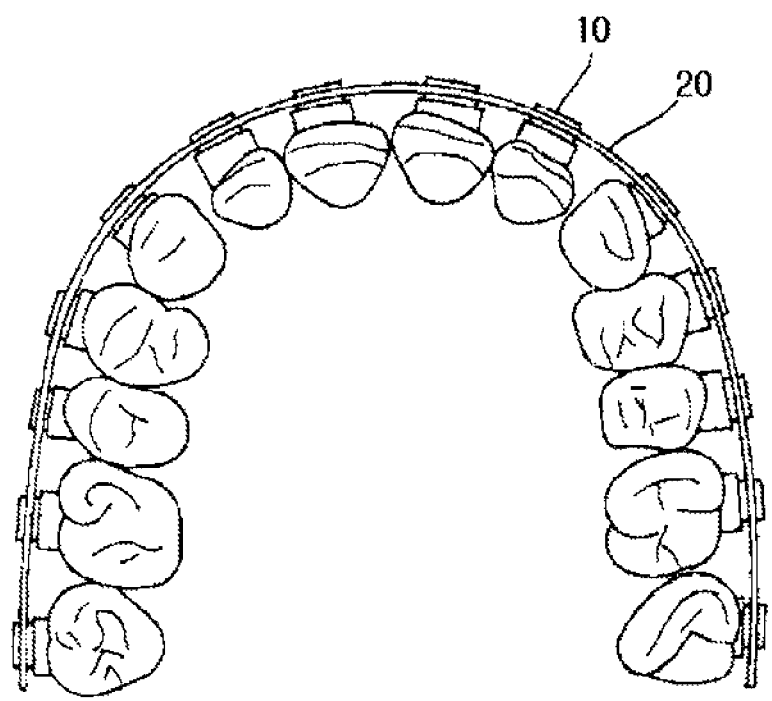
FIG. 1 is a schematic diagram illustrating an orthodontic state.

FIG. 1 is a schematic diagram illustrating an orthodontic state.

FIG. 1 illustrates a state in which a bracket 10 is mounted in each tooth for orthodontic and in which an orthodontic wire 20 is installed in the bracket 10.

Figure 4:
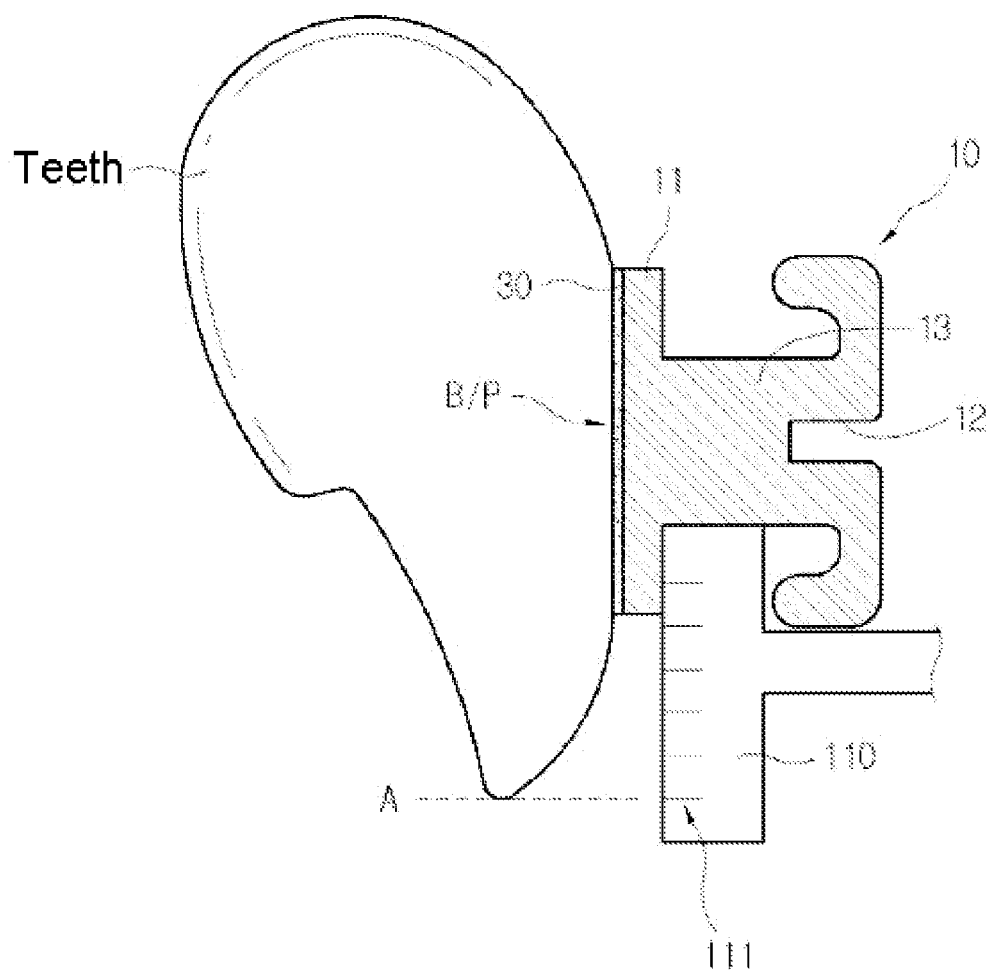
FIG. 4 is a diagram illustrating an example of measuring a height between a bracket stem and a teeth end portion illustrating a use example of the orthodontic bracket attaching tool of FIG. 2.

The bracket 10 is attached to a bracket attaching location B/P of teeth by an adhesive 30 (see FIG. 4). As shown in FIG. 4, the bracket 10 includes a bracket base 11 to which the adhesive 30 is attached, a slot 12 into which the orthodontic wire 20 is inserted, and a stem 13 disposed therebetween.

As the orthodontic wire 20 is inserted into the slot 12 (see FIG. 4) of the well attached bracket 10, a fixing force is transferred to teeth and thus a desired teeth movement can be performed.

When irregular teeth are straightened with a method of FIG. 1, after a surgical operation, teeth are regularly arranged and thus an aesthetic function, a pronunciation function, and a mastication function can be enhanced.

FIG. 1 illustrates a case of attaching the brackets 10 to a labial side, i.e., an outside lip (or cheek) of teeth and latching and extending the orthodontic wire 20 to the bracket 10 as a labial side orthodontic treatment.

However, the present invention is not limited thereto. That is, the present invention can be applied to an orthodontic treatment of the tongue side that is not shown from the outside.

In a method of performing orthodontic of FIG. 1, to accurately measure a bracket attaching location B/P to teeth and to attach the bracket 10 to the bracket attaching location B/P are the most important.

For this, conventionally, a separate gauge was used, but because the bracket 10 was attached to an inaccurate location or a surgical operation was uncomfortable, the present invention provides an orthodontic bracket attaching tool 100.

Because the orthodontic bracket attaching tool 100 according to the present invention has a more simple structure than that of the conventional art, a surgical operation is convenient, and because the bracket 10 can be attached by accurately setting an end portion of teeth and a height of the bracket 10, orthodontic efficiency can be improved.

Figure 2:
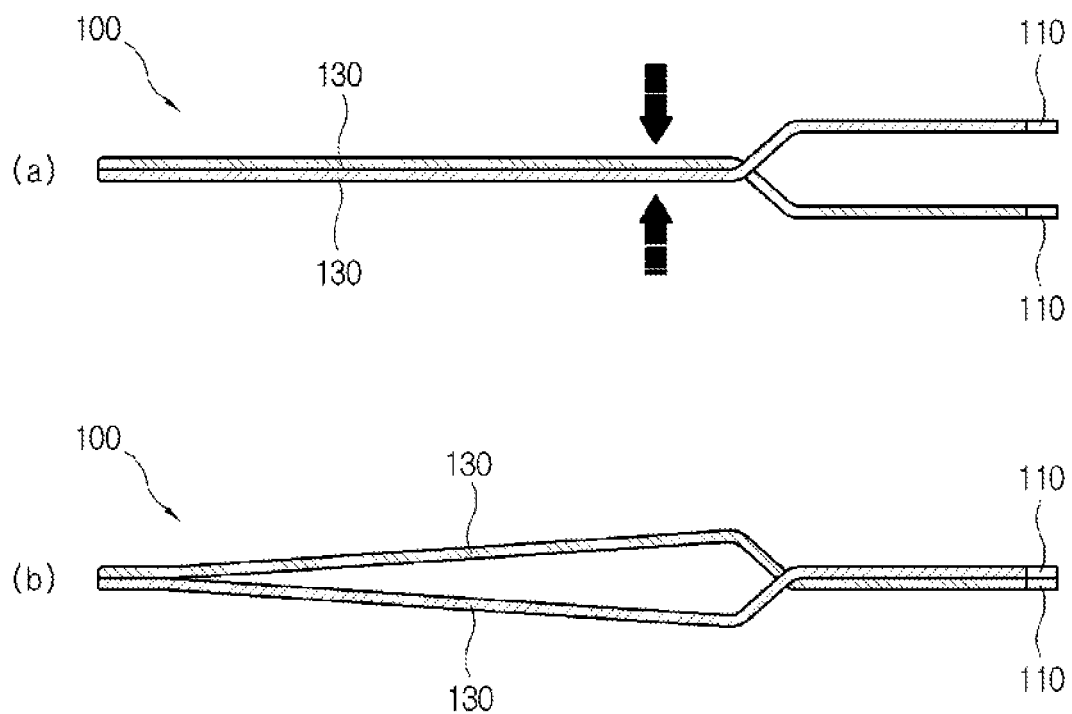
FIG. 2 is a side view illustrating an orthodontic bracket attaching tool according to a first exemplary embodiment of the present invention.
Figure 3:
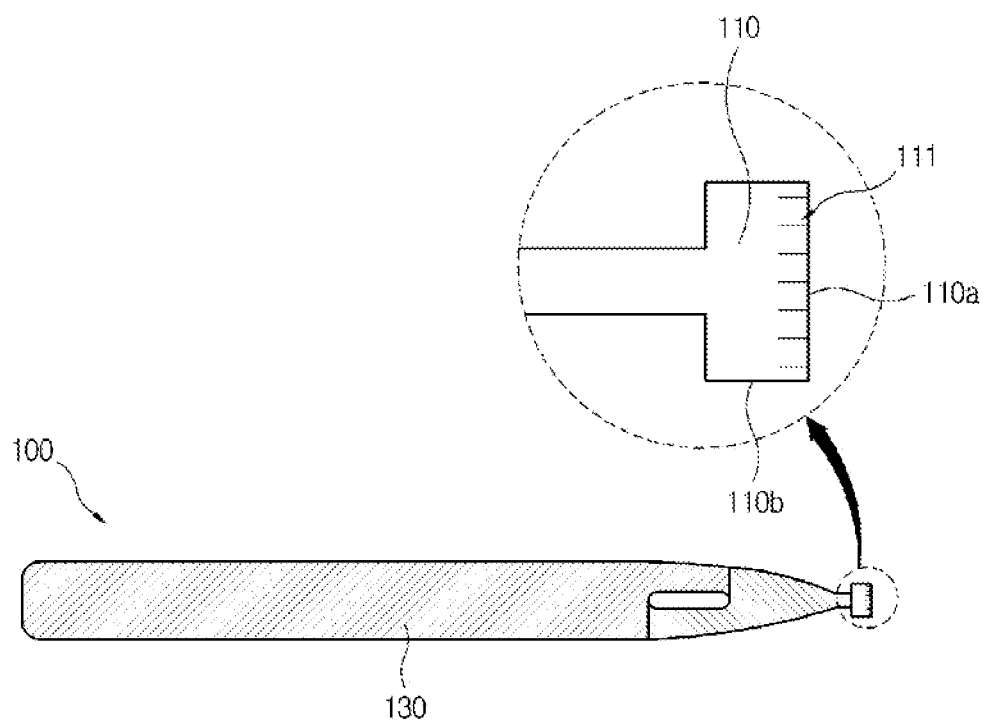
FIG. 3 is a top plan view illustrating the orthodontic bracket attaching tool of FIG. 2.

FIG. 2 is a side view illustrating an orthodontic bracket attaching tool according to a first exemplary embodiment of the present invention, FIG. 3 is a top plan view illustrating the orthodontic bracket attaching tool of FIG. 2, and FIG. 4 is a diagram illustrating a use example of the orthodontic bracket attaching tool of FIG. 2.

Referring to FIGS. 2 to 4, the orthodontic bracket attaching tool 100 of the present exemplary embodiment includes a pair of bracket holding portions 110 and a pair of handle portions 130 that manipulate a pair of bracket holding portions 110.

The pair of bracket holding portions 110 perform a function of holding the bracket 10 to be attached to teeth while approaching each other or separating from each other.

The pair of handle portions 130 are connected to the pair of bracket holding portions 110 to perform a function of manipulating the pair of bracket holding portions 110 to approach each other or separate from each other. A portion in which a surgical operator actually holds by a hand is a pair of handle portions 130.

For reference, the orthodontic bracket attaching tool 100 of the present exemplary embodiment is a tweezer type.

In the orthodontic bracket attaching tool 100 of a tweezer type, when approaching the pair of handle portions 130 by applying a force in an arrow direction shown in FIG. 2A, the pair of bracket holding portions 110 are separated from each other, and when removing a force applied to the pair of handle portions 130, the pair of bracket holding portions 110 approach each other, as shown in FIG. 2B.

The present invention can be applied to a pincette type orthodontic bracket attaching tool in which a pair of bracket holding portions 110 also approach each other, when a pair of handle portions 130 approach each other and in which a pair of bracket holding portions 110 are also separated from each other, when a pair of handle portions 130 are separated from each other.

As largely shown in FIG. 3, the circumferential side of the bracket holding portion 110 may have a straight shape, and adjacent circumferential sides may cross. In consideration of such a shape, an entire shape of the bracket holding portion 110 may have a quadrangular section shape.

When the bracket holding portion 110 has a quadrangular section shape and the circumferential side thereof has a straight shape, it is advantageous in view of horizontally maintaining the bracket 10 relative to teeth. That is, in a state that holds the bracket 10, because horizontality level may be adjusted through the circumferential side of a straight shape, it is advantageous in view of horizontally maintaining the bracket 10 relative to teeth.

In such a bracket holding portion 110, a height of the bracket 10 to an end portion A (see FIG. 4) of teeth, particularly, as a means that measures a height to the bracket attaching location B/P in which the bracket 10 is to be attached to the end portion A (see FIG. 4) of teeth, a scale 111 is used.

A scale 111 is used for measuring, and a unit thereof may be millimeter mm or centimeter cm. As shown in FIG. 3, such a scale 111 may be formed at one side of an end portion of the bracket holding portion 110, i.e., at a first side of the front side toward teeth.

By such a structure, after an adhesive is applied to the bracket, by applying a force in an arrow direction shown in FIG. 2A, in a state in which a pair of bracket holding portions 110 are separated each other, the bracket 10 is held between the pair of bracket holding portions 110 and is disposed at one side surface of teeth, as shown in FIG. 2A.

Thereafter, in order to locate the bracket 10 at a desired height of teeth, a location of the bracket 10 is adjusted at a surface of teeth using the scale 111 of the bracket holding portion 110.

That is, after the bracket holding portion 110 is disposed upward from a lower portion of the stem 13 of the bracket 10, the scale 111 measures a height to the bracket attaching location B/P to which the bracket 10 is to attach to the end portion A (see FIG. 4) of teeth using the scale 111 of the bracket holding portion 110.

When measurement is complete, by adjusting a location of the bracket 10, the bracket 10 is attached to teeth of the bracket attaching location B/P.

According to the present exemplary embodiment having such a structure and that can perform operation thereof, due to a simple structure, a surgical operation can be conveniently performed, measurement can be easily performed, and a measurement time can be shortened, and the bracket 10 can be attached by accurately setting an end portion A of teeth and a height of the bracket 10 and thus orthodontic efficiency can be improved.

Figure 5:
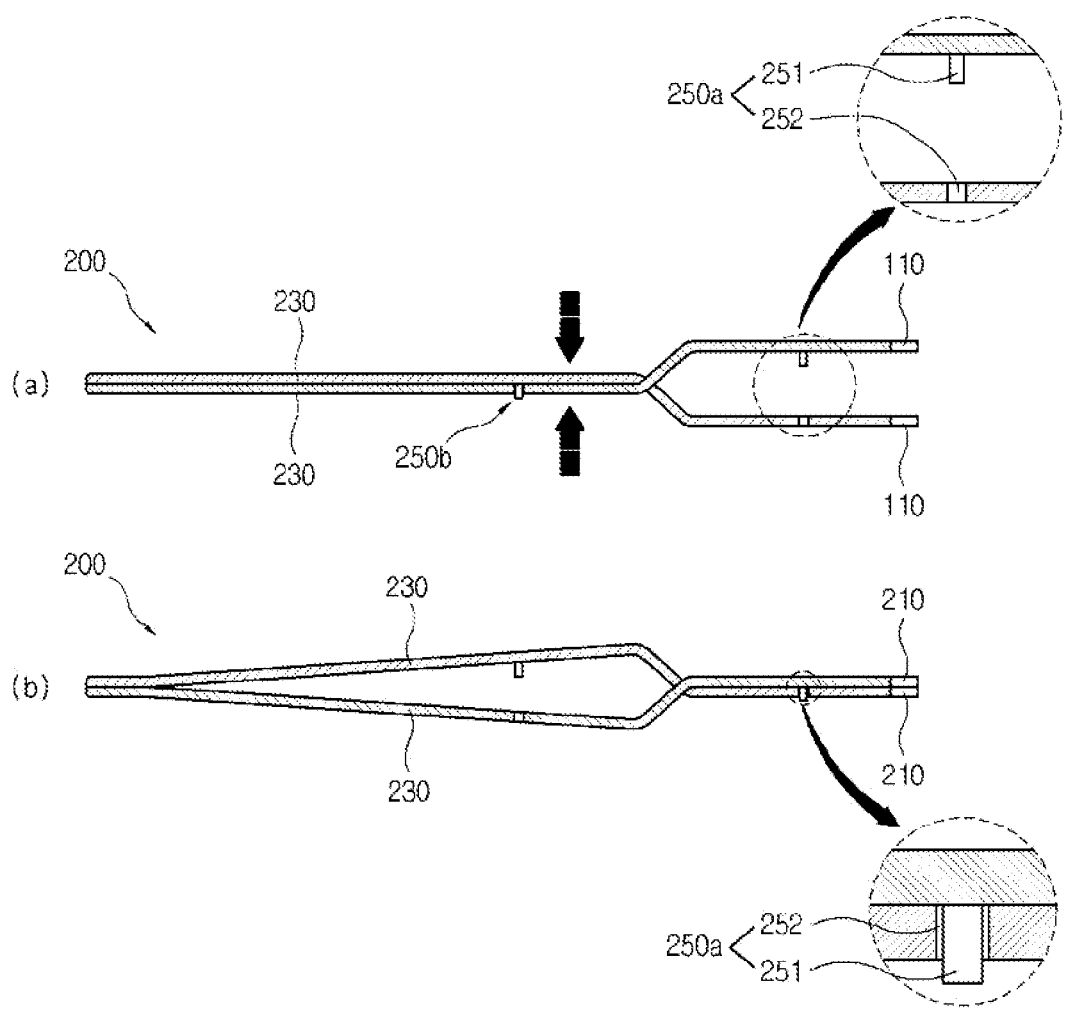
FIG. 5 is a side view illustrating an orthodontic bracket attaching tool according to a second exemplary embodiment of the present invention.

FIG. 5 is a side view illustrating an orthodontic bracket attaching tool according to a second exemplary embodiment of the present invention.

Referring to FIG. 5, in an orthodontic bracket attaching tool 200 of the present exemplary embodiment, when a bracket holding portion 210 approaches or separates, guides 250a and 250b that guide the bracket holding portion 210 to prevent the bracket holding portion 210 from deviating are further provided.

The guides 250a and 250b may include a first guide 250a provided in an area of a pair of bracket holding portions 210 and a second guide 250b provided in an area of a pair of handle portions 230.

The first and second guides 250a and 250b have only a location difference and may include a guide protrusion 251 and a guide groove 252 that guides the guide protrusion 251.

In this way, when the guides 250a and 250b are provided, an approaching operation of the bracket holding portion 210 can be stably guided and thus the bracket 10 can be stably held without a numerical value.

Figure 6:
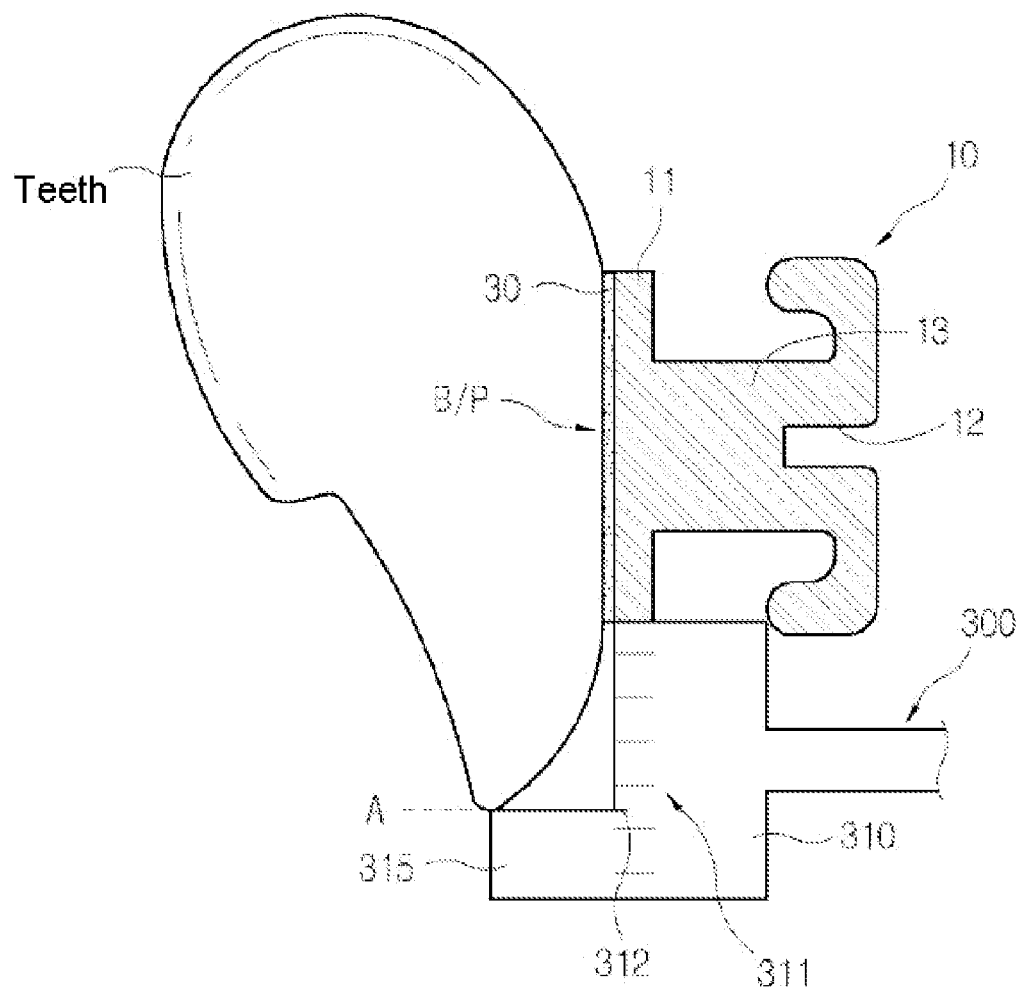
FIG. 6 illustrates a use example of an orthodontic bracket attaching tool according to a third exemplary embodiment of the present invention.

FIG. 6 illustrates a use example of an orthodontic bracket attaching tool according to a third exemplary embodiment of the present invention.

Referring to FIG. 6, in an orthodontic bracket attaching tool 300 of the present exemplary embodiment, a bracket holding portion 310 has a polygonal section shape having a latch jaw 315 disposed at an end portion of teeth to form a reference of measurement, for example, a protruded shape (structure), i.e., an L-shaped section shape in which an area of the latch jaw 315 is protruded to one side.

In the bracket holding portion 310, as a means that measures a height to a bracket attaching location B/P in which a bracket 10 is to be attached to an end portion A of teeth, i.e., a height from a lower portion of a bracket base 11 to an end portion A of teeth, a scale 311 is formed.

In this case, in the bracket holding portion 310, an end portion indication portion 312 that indicates the end portion A of teeth may be formed, thereby accurately and easily measuring a height. That is, when putting the latch jaw 315 at the end portion A of teeth, a height from a base of the bracket base 11 to an end portion of teeth can be easily measured.

Figure 7:
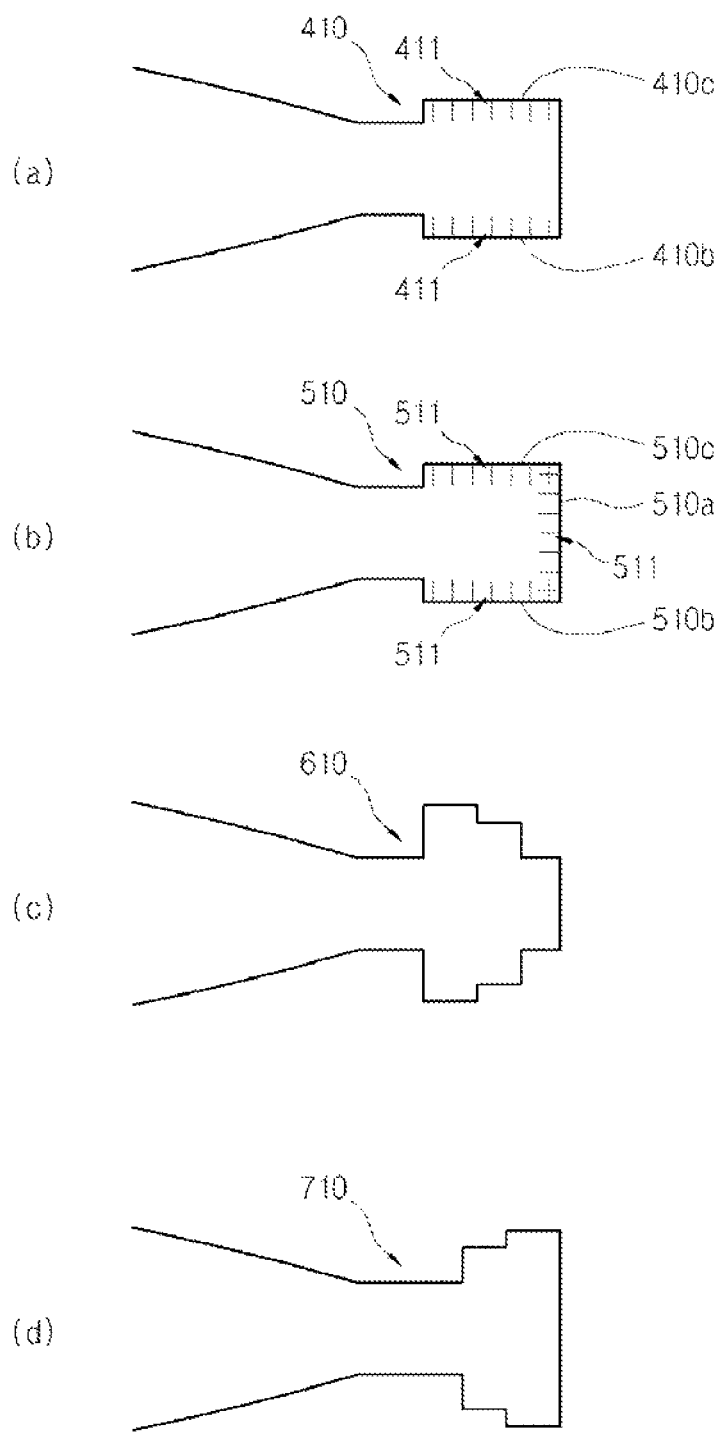
FIG. 7 illustrates various modified examples of an orthodontic bracket attaching tool.

FIG. 7 illustrates various modified examples of an orthodontic bracket attaching tool.

FIG. 7A illustrates a case in which a scale 411 is formed in both of two opposing sides 410b and 410c of a bracket holding portion 410, and FIG. 7B illustrates a case in which a scale 511 is formed in the entire of circumferential sides 510a-510c of a bracket holding portion 510.

FIGS. 7C and 7D illustrate a case in which bracket holding portions 610 and 710 have a stepped polygonal shape having a reducing or enlarging width as advancing a free end portion of the bracket holding portions 610 and 710 instead of a quadrangular section shape.

Even if the bracket holding portions 610 and 710 have the same shape as that of FIGS. 7A to 7D or a shape similar to that of FIGS. 7A to 7D, an effect of the present invention can be provided. For example, the bracket holding portions 610 and 710 may have a protruded shape described in FIG. 6.

For reference, a scale is not shown in FIGS. 7C and 7D, but a scale may be formed in FIGS. 7C and 7D.

Further, the foregoing exemplary embodiment illustrates a tweezer type orthodontic bracket attaching tool, but an orthodontic bracket attaching tool according to the present invention can be applied to a pincette type.

Although exemplary embodiments of the present invention have been described in detail hereinabove, it should be clearly understood that many variations and modifications of the basic inventive concepts herein taught which may appear to those skilled in the present art will still fall within the spirit and scope of the present invention, as defined in the appended claims.

DESCRIPTION OF SYMBOLS

10: bracket 11: bracket base
12: slot 13: stem
20: orthodontic wire 30: adhesive
100: orthodontic bracket attaching tool 110: bracket holding portion
111: scale 130: handle portion

What is claimed is:
1. An orthodontic bracket attaching tool, comprising:
a pair of bracket holding portions that hold a bracket to be attached to a tooth while approaching each other or separating from each other; and
a pair of handle portions connected to the pair of bracket holding portions to manipulate the bracket holding portions to approach each other or separate from each other, wherein in an end portion of at least one of the pair of bracket holding portions, a scale that measures a height of the bracket to an end portion of the tooth is formed; and wherein each of the bracket holding portions has a quadrangular-shaped section and the circumferential side of each of the pair of bracket holding portions has a straight shape.

2. The orthodontic bracket attaching tool of claim 1, wherein an end portion of each of the pair of bracket holding portions has a polygonal section shape in which a latch jaw that forms a measurement reference is formed, and in the pair of bracket holding portions, an end portion indication portion configured to indicate an end portion of the tooth is formed.

3. The orthodontic bracket attaching tool of claim 1, wherein the scale is formed in at least one side of the bracket holding portion in which the scale is formed.

4. The orthodontic bracket attaching tool of claim 1, wherein said orthodontic bracket attaching tool is suitable for use with a bracket which comprises:
a bracket base to which an adhesive is attached:
a slot into which an orthodontic wire is inserted; and
a stem disposed between the bracket base and the slot, wherein the bracket holding portion in which the scale is formed measures a distance between one side of the bracket base or the stem and the end portion of the tooth.

5. The orthodontic bracket attaching tool of claim 1, further comprising a guide that guides an approaching or separating operation of the pair of bracket holding portions.

6. The orthodontic bracket attaching tool of claim 5, wherein the guide comprises:
a first guide provided in an area of the pair of bracket holding portions; and
a second guide provided in an area of the pair of handle portions.

7. The orthodontic bracket attaching tool of claim 6, wherein both the first and second guides each comprise:
a guide protrusion; and
a guide groove that guides the guide protrusion.

8. The orthodontic bracket attaching tool of claim 1, wherein one of the pair of bracket holding portions has a stepped polygonal shape having a plurality of steps, wherein successive steps, taken in a direction toward an end portion of the bracket holding portion, are wider or narrower than preceding steps; or a protruded shape having a protruded one side of the pair of bracket holding portions.

* * * * *